United States Patent
Nakata et al.

(10) Patent No.: US 12,332,175 B2
(45) Date of Patent: Jun. 17, 2025

(54) OPTICAL MEASUREMENT CELL, OPTICAL ANALYZER, WINDOW FORMING MEMBER, AND METHOD OF MANUFACTURING OPTICAL MEASUREMENT CELL

(71) Applicant: HORIBA STEC, Co., Ltd., Kyoto (JP)

(72) Inventors: Yoshiaki Nakata, Kyoto (JP); Masakazu Minami, Kyoto (JP); Yuhei Sakaguchi, Kyoto (JP); Toru Shimizu, Kyoto (JP); Takeshi Akamatsu, Kyoto (JP)

(73) Assignee: HORIBA STEC, CO., LTD., Kyoto (JP)

( * ) Notice: Subject to any disclaimer, the term of this patent is extended or adjusted under 35 U.S.C. 154(b) by 370 days.

(21) Appl. No.: 18/087,006

(22) Filed: Dec. 22, 2022

(65) Prior Publication Data

US 2023/0228679 A1  Jul. 20, 2023

(30) Foreign Application Priority Data

Jan. 14, 2022 (JP) ................................ 2022-004415

(51) Int. Cl.
*G01N 21/61* (2006.01)
*G01N 33/00* (2006.01)

(52) U.S. Cl.
CPC ......... *G01N 21/61* (2013.01); *G01N 33/0027* (2013.01); *G01N 33/007* (2013.01)

(58) Field of Classification Search
CPC ............... G01N 21/05; G01N 21/3504; G01N 2021/0389
USPC ......................................................... 356/437
See application file for complete search history.

(56) References Cited

U.S. PATENT DOCUMENTS

| | | | | |
|---|---|---|---|---|
| 4,278,195 A | * | 7/1981 | Singh | H01L 24/83 228/123.1 |
| 5,796,109 A | * | 8/1998 | Frederick | G01T 1/202 250/361 R |
| 2017/0052115 A1 | * | 2/2017 | Hayashi | G01N 21/05 |

* cited by examiner

*Primary Examiner* — Nathaniel T Woodward
(74) *Attorney, Agent, or Firm* — Greenblum & Bernstein, P.L.C.

(57) ABSTRACT

In order to prevent cracking of a window material in manufacturing an optical measurement cell that satisfies various performances required for airtightness, heat resistance, and the like by atomic diffusion bonding, an optical measurement cell into which a sample is introduced includes a light transmission window through which light is transmitted, and includes a window material forming the light transmission window, and a flange member to which the window material is bonded via a metal thin film, and a ratio of a thermal expansion coefficient of the flange member to a thermal expansion coefficient of the window material is 0.5 times or more and 1.5 times or less.

6 Claims, 7 Drawing Sheets

OPTICAL MEASUREMENT CELL, OPTICAL ANALYZER, WINDOW FORMING MEMBER, AND METHOD OF MANUFACTURING OPTICAL MEASUREMENT CELL

BACKGROUND

Technical Field

The present invention relates to an optical measurement cell, an optical analyzer using the optical measurement cell, and the like.

Related Art

Conventionally, for example, an optical measurement cell used in an optical analyzer such as NDIR is considered to have a configuration in which a window forming member having a window material is attached to a cell main body as shown in JP 2017-40655 A.

In a case where an O-ring is used as a structure for airtightly fixing the window material in the window forming member, a slight amount of a gas leaks from a gap between the O-ring and a sealed portion or through the O-ring itself, and highly airtight sealing cannot be performed. Furthermore, when the gas has reactivity, the O-ring may be deteriorated by the gas.

It is also conceivable to use a metal O-ring instead of this O-ring, but in this case, even if the sealing property can be temporarily maintained when a linear load at the time of sealing is small, leakage occurs when a thermal cycle is repeated. On the other hand, when the linear load is increased, the window material is broken.

Figure 7:
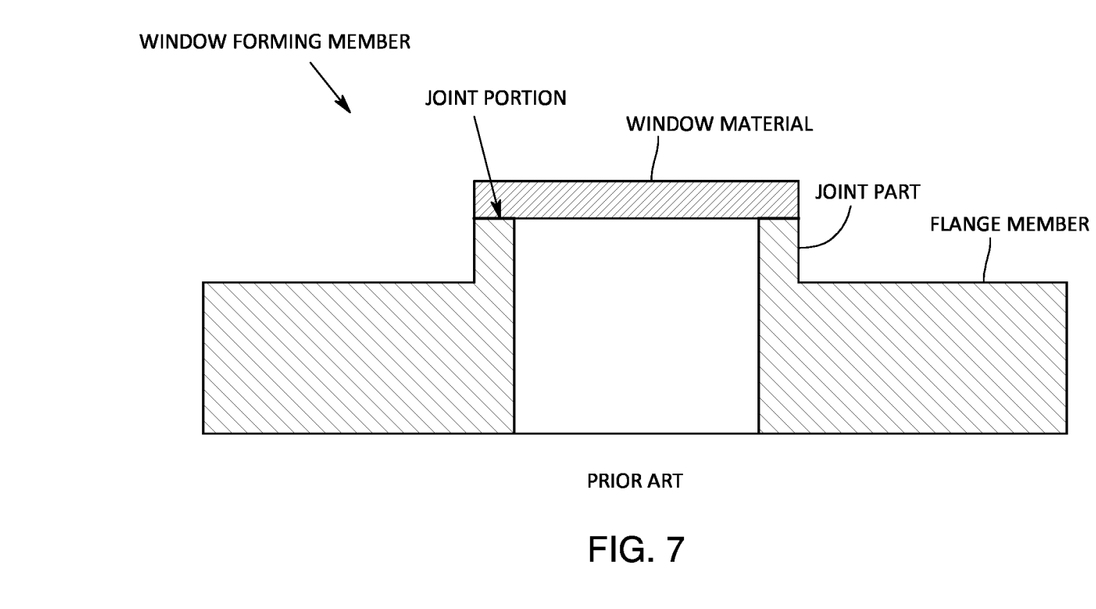
FIG. 7 is a cross-sectional view illustrating a structure of a conventional window forming member.

Therefore, as a structure for ensuring airtightness, as illustrated in FIG. 7, a structure in which a joint part formed on a flange member is bonded to a flat part (principal surface) of a window material is considered.

A joint portion having this structure is required not only to have a very low leak rate but also to have heat resistance to withstand a temperature (200° C.) during the process, and is also required to have various performances such as the need to prevent cracking of the window material in the manufacturing process.

Under such circumstances, the inventors of the present application have studied, for example, an adhesive or brazing as a method of airtightly bonding the window material to the joint part of the flange member, but have concluded that it is extremely difficult to satisfy all of the various required performances by any method.

Therefore, as a result of further intensive studies, the inventors of the present application have found a possibility that all the required various performances can be satisfied by bonding the window material and the joint part by atomic diffusion bonding.

However, when a difference in thermal expansion coefficient between the flange member and the window material is large, for example, when a flange member made of stainless steel is used as the flange member and a window material made of ZnSe is used as the window material, there arises a problem that the window material is broken due to, for example, bending of the window material or thermal deformation of the flange member due to thermal influence during the process.

PRIOR ART DOCUMENT

Patent Document

JP 2017-40655 A

SUMMARY

Therefore, the present invention has been made to solve the above-described problems at once, and a main object of the present invention is to prevent cracking of the window material in manufacturing an optical measurement cell satisfying various required performances such as airtightness and heat resistance by atomic diffusion bonding.

That is, an optical measurement cell according to the present invention is an optical measurement cell including a light transmission window through which light is transmitted, and into which a sample is introduced, the optical measurement cell including: a window material forming the light transmission window; and a flange member to which the window material is bonded via a metal thin film, in which a ratio of a thermal expansion coefficient of the flange member to a thermal expansion coefficient of the window material is 0.5 times or more and 1.5 times or less.

According to the optical measurement cell configured as described above, since the window material is bonded to the flange member via the metal film, in other words, the window material is atomically diffusion-bonded to the flange member, various performances such as airtightness and heat resistance required therebetween can be satisfied.

Moreover, since the ratio of the thermal expansion coefficient of the flange member to the thermal expansion coefficient of the window material is 0.5 times or more and 1.5 times or less, and the thermal expansion coefficients of both members are close to each other, cracking of the window material can be prevented.

As a specific embodiment, an embodiment in which the window material is made of zinc selenide or sapphire and the flange member is made of titanium or stainless invar, and an embodiment in which the window material is made of barium fluoride and the flange member is made of stainless or nickel can be mentioned. Note that an aspect in which the window material made of zinc selenide or barium fluoride is used contributes to analysis using light in a long wavelength range (for example, infrared rays of 7 μm or more).

Furthermore, an optical analyzer according to the present invention includes: the optical measurement cell mentioned above; a light irradiation unit that irradiates the optical measurement cell with light; a light detection unit that detects light transmitted through the optical measurement cell; and a concentration calculation unit that calculates a component concentration in the sample using a light intensity signal obtained by the light detection unit.

Moreover, a method of manufacturing an optical measurement cell according to the present invention is a method of manufacturing an optical measurement cell including a light transmission window through which light is transmitted and into which a sample is introduced, the light transmission window including a window material and a flange member supporting the window material, and a ratio of a thermal expansion coefficient of the flange member to a thermal expansion coefficient of the window material being 0.5 times or more and 1.5 times or less, the method including performing atomic diffusion bonding of the window material and the flange member.

In addition, a window forming member according to the present invention is a window forming member used in an optical measurement cell into which a sample is introduced, the window forming member including: a window material forming a light transmission window through which light is transmitted; and a flange member to which the window material is bonded via a metal thin film, in which a ratio of a thermal expansion coefficient of the flange member to a thermal expansion coefficient of the window material is 0.5 times or more and 1.5 times or less.

According to the optical analyzer, the method of manufacturing the optical measurement cell, and the window forming member according to the present invention, the same operational effects as those of the optical measurement cell described above can be obtained.

According to the present invention described above, it is possible to prevent cracking of the window material while manufacturing the optical measurement cell that satisfies various required performances such as airtightness and heat resistance by atomic diffusion bonding.

DETAILED DESCRIPTION

Hereinafter, a gas analyzer according to an embodiment of the present invention will be described with reference to the drawings.

1. Overall Configuration

A gas analyzer 100 of the present embodiment analyzes components in a sample gas using, for example, a non-dispersive infrared absorption method (NDIR). Note that, as the sample gas, a material gas used in a semiconductor manufacturing process, an exhaust gas discharged from an internal combustion engine, and the like can be considered.

Figure 1:
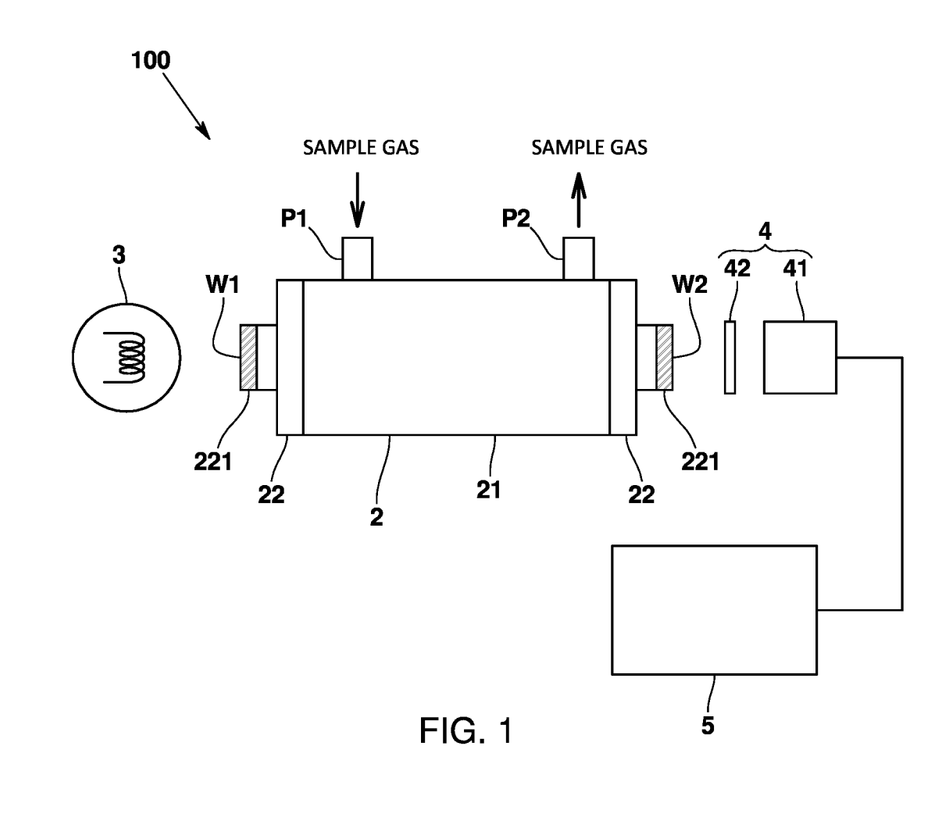
FIG. 1 is an overall schematic view of a gas analyzer according to an embodiment of the present invention.

Specifically, as illustrated in FIG. 1, the gas analyzer 100 includes an optical measurement cell 2 into which a sample gas is introduced, a light irradiation unit 3 that irradiates the optical measurement cell 2 with infrared light, a light detection unit 4 that detects the infrared light having passed through the optical measurement cell 2, and a concentration calculation unit 5 that calculates a component concentration in the sample gas using a light intensity signal obtained by the light detection unit 4.

The optical measurement cell 2 has a pair of light transmission windows W1, W2 through which infrared light is transmitted, and is a flow cell type in which the sample gas is introduced from an introduction port P1 and the sample gas is led out from a lead-out port P2.

Specifically, the optical measurement cell 2 includes a cell body 21 provided with the introduction port P1 and the lead-out port P2, and window forming members 22 fixed to the cell body 21 and having window materials 221 forming the light transmission windows W1, W2. Note that the detailed structure of the window forming members 22 of the optical measurement cell 2 will be described later.

The light irradiation unit 3 irradiates the optical measurement cell 2 with infrared light, and is, for example, an infrared lamp. In addition, an LED that emits infrared light may be used. The infrared light emitted from the light irradiation unit 3 passes through one light transmission window W1 of the optical measurement cell 2, passes through an internal space of the optical measurement cell 2, passes through the other light transmission window W2, and is detected by the light detection unit 4.

The light detection unit 4 detects the infrared light that has passed through the optical measurement cell 2, and includes a light detector 41 that detects the infrared light that has passed through the other light transmission window W2 of the optical measurement cell 2, and a wavelength selection filter 42 that is provided on an optical path between the other light transmission window W2 and the light detector 41 and allows only a part of wavelengths of the infrared light to pass. A light intensity signal obtained by the light detector 41 is output to the concentration calculation unit 5.

The concentration calculation unit 5 calculates the concentration of a predetermined component in the sample gas using the light intensity signal obtained by the light detector 41. Specifically, the concentration calculation unit 5 calculates an absorbance from the light intensity signal, and obtains a partial pressure of a predetermined component in the sample gas based on the absorbance and a calibration curve created in advance and recorded in a memory. Then, the concentration calculation unit 5 calculates the concentration of the predetermined component (=the partial pressure of the predetermined component/a total pressure of the sample gas) based on the total pressure of the sample gas in the optical measurement cell 2 measured by a pressure gauge (not illustrated) provided in the optical measurement cell 2 or pipes before and after the optical measurement cell 2. Note that a function of the concentration calculation unit 5 is exerted by a computer including, for example, a CPU, a memory, an AD converter, an input/output interface, and the like.

2. Detailed Structure of Window Forming Member 22 of Optical Measurement Cell 2

Next, a detailed structure of the window forming member 22 of the optical measurement cell 2 will be described.

Note that, since the detailed structure of the window forming member 22 forming the one light transmission window W1 is the same as or similar to the detailed structure of the window forming member 22 forming the other light transmission window W2, the detailed structure of the window forming member 22 forming the one light transmission window W1 will be described below as a representative.

Figure 2A:
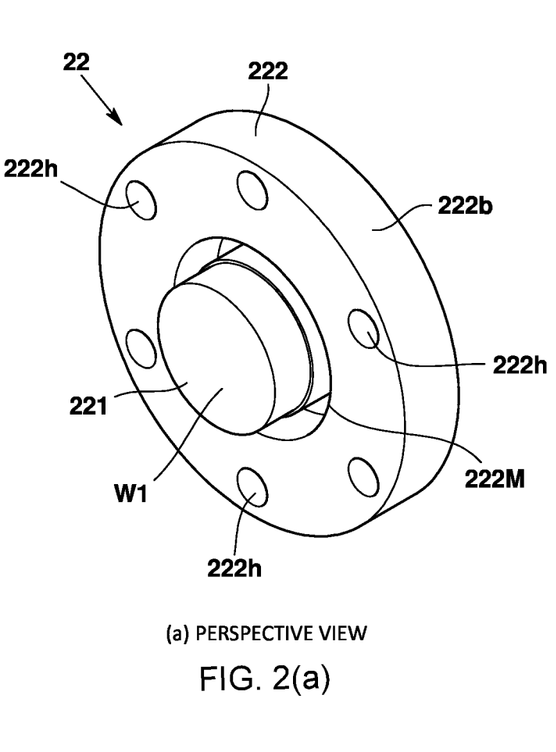
FIG. 2(a) is a perspective view and FIG. 2(b) is a front view illustrating a structure of a window forming member of the embodiment.
Figure 2B:
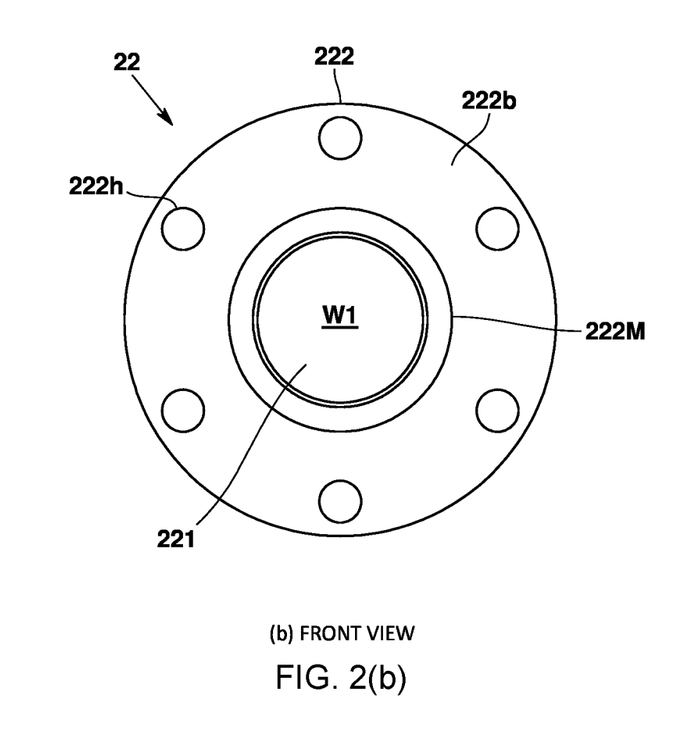
Figure 3:
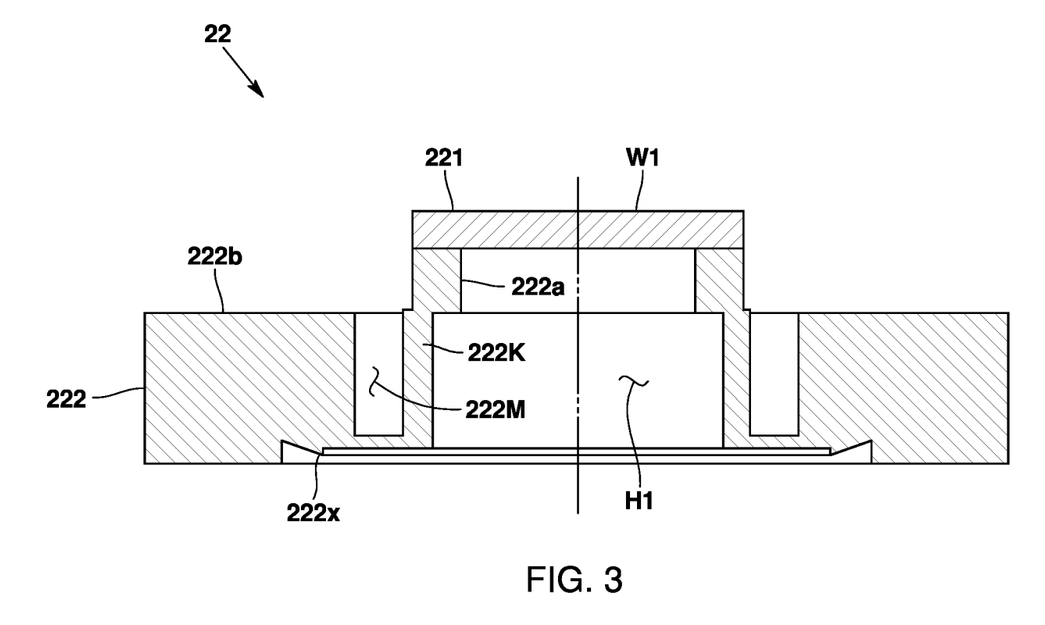
FIG. 3 is a cross-sectional view illustrating a structure of the window forming member of the embodiment.

As illustrated in FIGS. 2 and 3, the window forming member 22 includes the flat plate-shaped window material 221 forming the light transmission window W1 and a flange member 222 supporting the window material 221 by bonding the window material 221, and is also referred to as a flanged observation window. Note that the term "flat plate shape" as used herein refers to a concept including not only a flat plate without any bend but also a spherical or aspherical plano-convex lens shape, a wedge shape with a wedge angle, and the like.

The window material 221 is formed of a material that transmits infrared light, and is a flat plate having a circular shape in plan view. The window material 221 of the present embodiment transmits infrared light having a long wavelength of 7 μm or more, and is formed of zinc selenide (ZnSe) in the present embodiment.

As particularly illustrated in FIG. 3, the flange member 222 includes a tubular joint support part 222a that supports the window material 221, and a flange part 222b provided continuously to the joint support part 222a so as to surround the window material 221. Furthermore, a passage hole H1 through which infrared light having passed through the window material 221 passes is formed in a central part of the flange member 222. Moreover, in the present embodiment, the joint support part 222a and the flange part 222b are integrally formed.

The joint support part 222a supports the principal surface (planar part) of the window material 221, and has a cylindrical shape in the present embodiment.

The flange part 222b is provided with the joint support part 222a on one surface thereof, and has an annular shape in the present embodiment. The flange part 222b is attached to the cell body 21 via, for example, a metal gasket (not illustrated), and an ICF-standard knife edge part 222x is formed on an attachment surface of the flange part 222b to the cell body 21. Furthermore, a plurality of through holes 222h for screwing to the cell body 21 are formed in the flange part 222b in a circumferential direction.

In the above-described configuration, as a method of airtightly bonding the window material 221 and the flange member 222, a method of bonding these members by, for example, an adhesive, brazing, or the like is considered.

However, when the adhesive is used, degassing from the adhesive, deterioration due to a corrosive gas, cracking of the window material 221 due to a difference in thermal expansion coefficient between the window material 221 and the flange member 222, and the like are concerned.

Furthermore, in the case of brazing, if silver, copper, or the like is contained in the brazing material, metal contamination occurs in the semiconductor process, and the brazing material cannot be used, and in that case, there is no brazing material suitable for the window material 221 made of zinc selenide. Even if there is a usable brazing material, there is a concern about cracking of the window material 221 similarly to the adhesive.

Therefore, the window forming member 22 of the present embodiment is configured by bonding the window material 221 and the flange member 222 by atomic diffusion bonding.

The atomic diffusion bonding is a method in which a metal film is interposed between joint surfaces of two members and these members are bonded by pressurizing these members. In this embodiment, the window material 221 and the flange member 222 are pressure-bonded via a metal thin film M such as an Au film having a thickness of, for example, about several hundred nm.

By the way, as described above, since the window forming member 22 formed by atomic diffusion bonding of the window material 221 and the flange member 222 is affected by heat during the process, for example, when a difference between the thermal expansion coefficient of the window material 221 and the thermal expansion coefficient of the flange member 222 is large, the window material 221 may be bent or the flange member 222 may be thermally deformed, and the window material 221 may be cracked.

Therefore, the window forming member 22 of the present embodiment is configured such that a ratio of the thermal expansion coefficient of the flange member 222 to the thermal expansion coefficient of the window material 221 is 0.5 times or more and 1.5 times or less, and more preferably, the ratio is 0.66 times or more and 1.5 times or less.

Note that the thermal expansion coefficient described below is a value obtained by measuring a length of the sample when a temperature is changed, a known value described in, for example, a scientific chronological table, a value measured based on, for example, the following standard, or the like.

JIS K 0129 Thermal Analysis General Rules

More specifically, since the window material 221 of the present embodiment is made of zinc selenide (ZnSe) and has a thermal expansion coefficient of $7.1 \times 10^{-6}$/K as described above, in view of the above-described ratio, the flange member 222 of the present embodiment is made of titanium and has a thermal expansion coefficient of $8.9 \times 10^{-6}$/K.

Note that an experimental result has been obtained in which when Hastelloy having a thermal expansion coefficient of $11.3 \times 10^{-6}$/K is used as the flange member 222, the window material 221 is cracked.

Next, an example of a method of bonding the window material 221 and the flange member 222 described above will be described with reference to FIG. 4.

Figure 4:
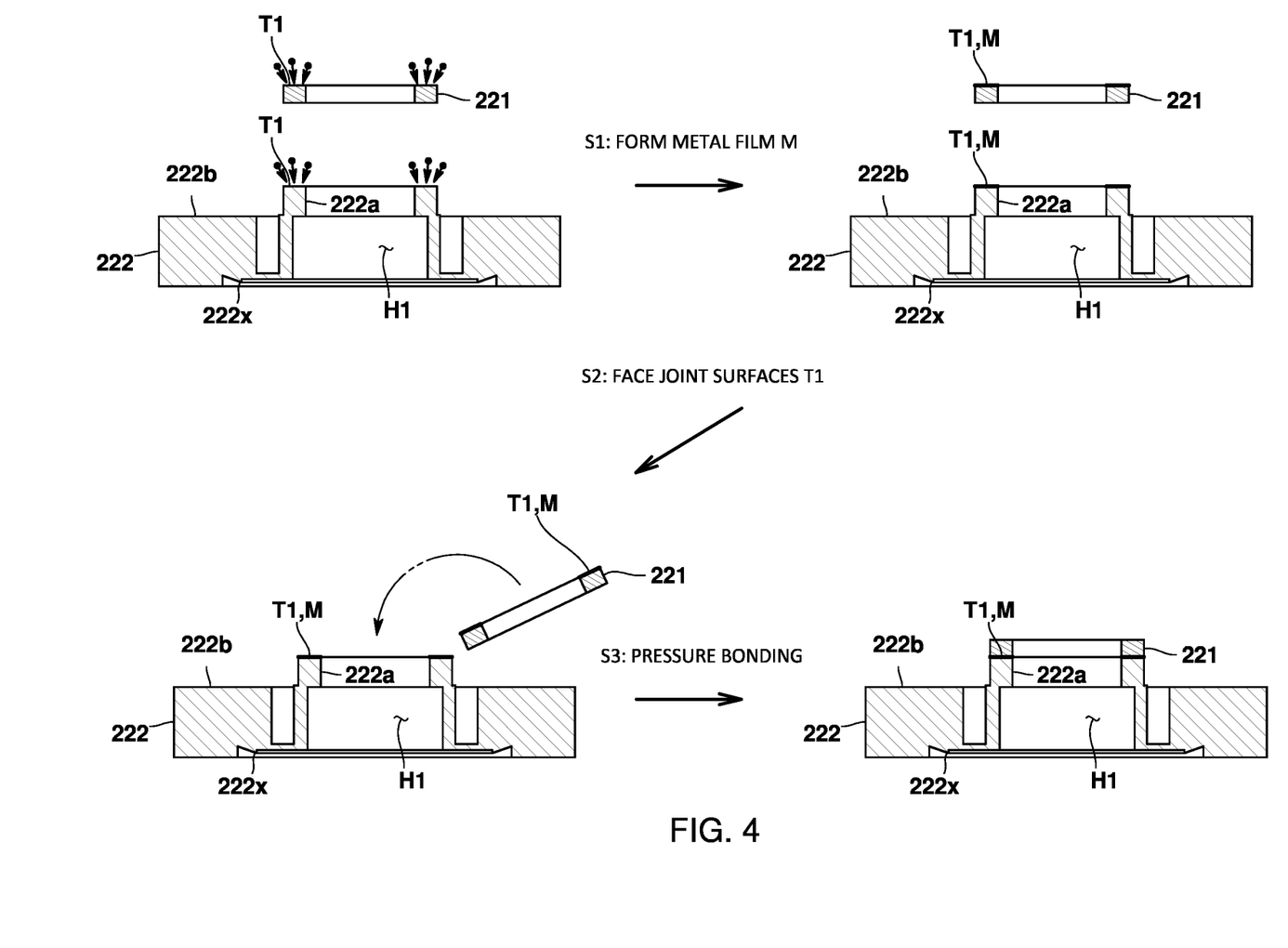
FIG. 4 is a schematic diagram illustrating an example of a method of forming the window forming member of the embodiment.

First, as illustrated in FIG. 4, a metal thin film M is formed on each of joint surfaces T1 that are facing surfaces of the window material 221 and the flange member 222 (S1). In the present embodiment, the metal thin film M is formed by sputtering on the joint surface T1.

Then, the joint surfaces T1 provided with the metal thin films M face each other (S2), and the window material 221 and the flange member 222 are pressurized in opposing directions to perform atomic diffusion bonding (pressure bonding) of the window material 221 and the flange member 222 (S3).

In this manner, the window material 221 and the flange member 222 are atomically diffusion-bonded to form the window forming member 22.

In the window forming member 22 configured as described above, as illustrated in FIG. 3, thermal stress due to thermal expansion of the flange part 222b is less likely to be applied to a joint portion between the window material 221 and the joint support part 222a.

Specifically, an annular groove 222M is formed in a surface of the flange part 222b on a side of the joint support part 222a (a surface opposite to an attachment surface) so as to surround the joint support part 222a. Here, the groove 222M has an annular shape formed coaxially with the joint support part 222a. It is conceivable that a depth of the groove 222M is, for example, half or more of a plate thickness of the flange part 222b.

Here, a wall thickness (thickness) of an inner wall part 222K located inside the groove 222M in the flange member 222 is configured to be smaller than a wall thickness (thickness) of the joint support part 222a. As described above, by increasing the wall thickness of the joint support part 222a and decreasing the wall thickness of the inner wall part 222K, it is possible to make it difficult to apply thermal stress due to thermal expansion of the flange part 222b to the joint portion between the window material 221 and the joint support part 222a while increasing a joint area between the window material 221 and the joint support part 222a.

Moreover, by providing the groove 222M in this manner, distortion of the flange member 222 generated when the flange member 222 is attached to another member with, for example, a screw or the like can be made less likely to be transmitted to the joint portion between the window material 221 and the joint support part 222a.

3. Effects of Present Embodiment

According to the gas analyzer 100 of the present embodiment configured as described above, since the window material 221 is atomically diffusion-bonded to the flange member 222, it is possible to satisfy various performances such as airtightness and heat resistance required therebetween.

Moreover, since the ratio of the thermal expansion coefficient of the flange member 222 to the thermal expansion coefficient of the window material 221 is close, the window material 221 can be prevented from cracking.

Figure 5:
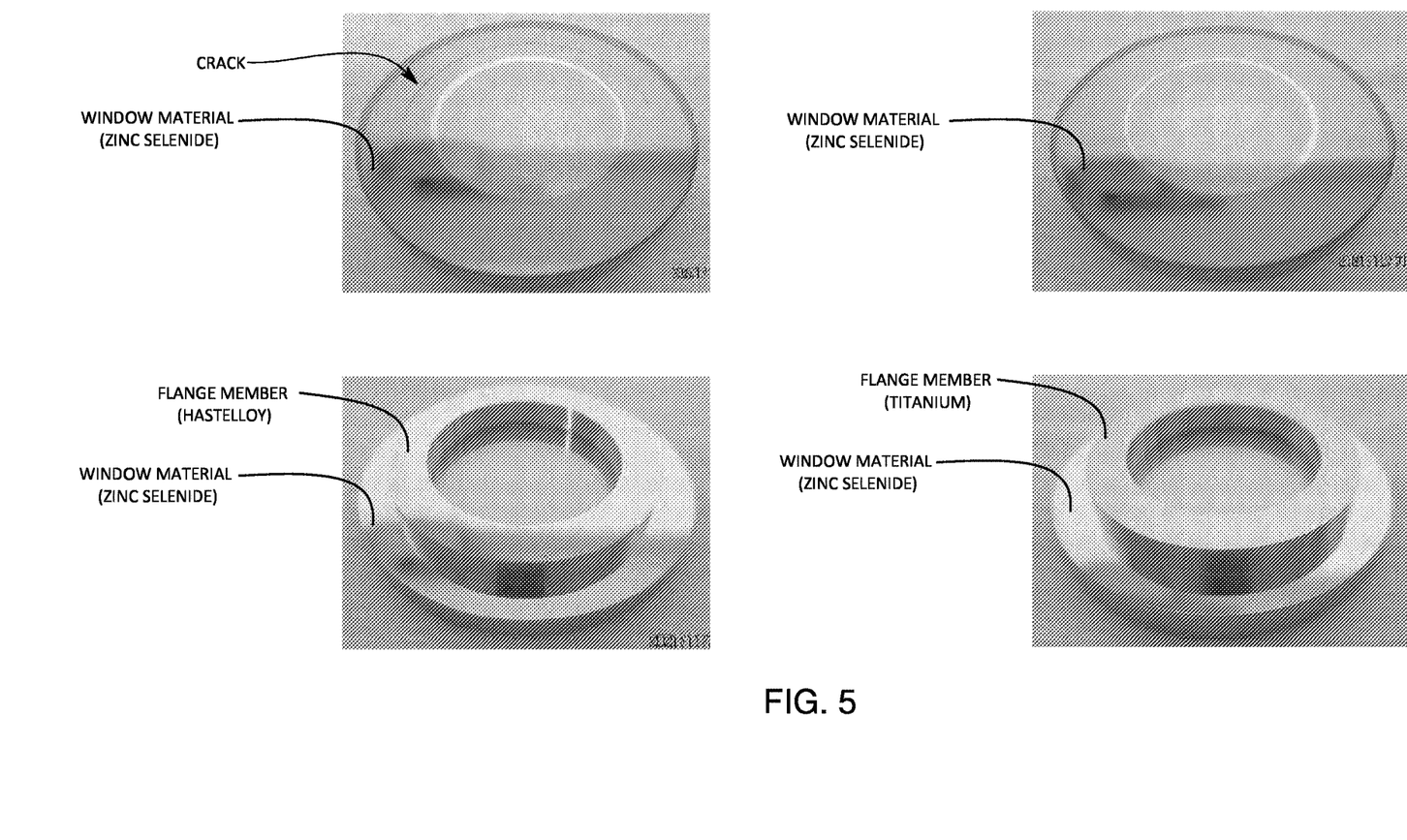
FIG. 5 is a photograph illustrating an experimental result using the window forming member of the embodiment.

Here, the photographs illustrated in FIG. 5 show results of an experiment as to whether or not the window material is cracked when the window material is atomically diffusion-bonded to the flange member at 120° C. and then cooled to room temperature.

As can be seen from the experimental results, in the case where the window material is made of zinc selenide and the flange member is made of Hastelloy (left side in FIG. 5), cracks are generated in the window material due to a difference in thermal expansion coefficient between these materials, whereas in the case where the window material is made of zinc selenide and the flange member is made of titanium as in the present embodiment (right side in FIG. 5), cracks are not generated in the window material.

Furthermore, since the window material 221 is made of zinc selenide having a low thermal expansion coefficient, it contributes to analysis in a long wavelength range (for example, 7 µm or more).

4. Other Embodiments

Figure 6:
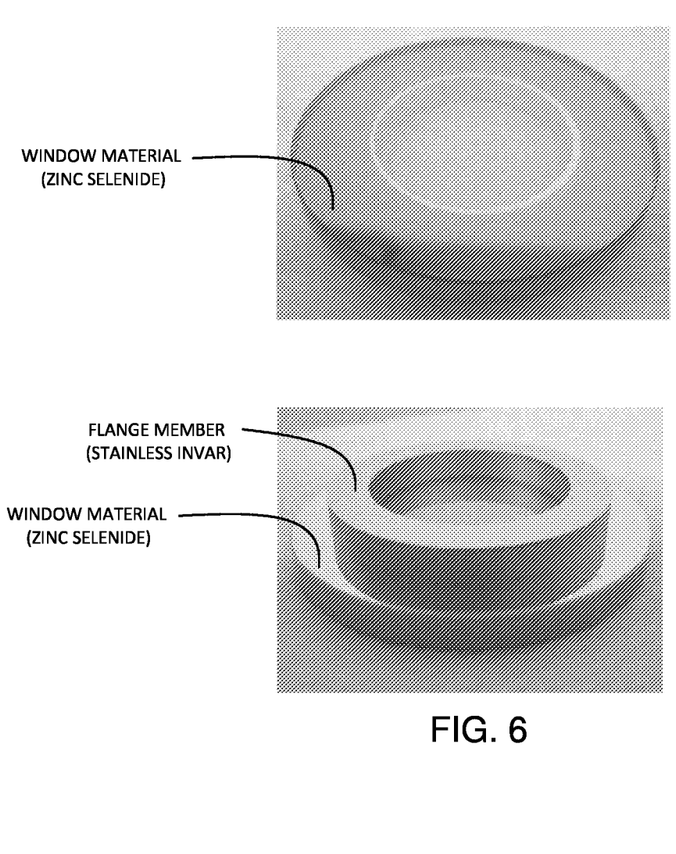
FIG. 6 is a photograph illustrating an experimental result using a window forming member of another embodiment.

For example, in the above embodiment, the window forming member 22 is configured using the window material 221 made of zinc selenide and the flange member 222 made of titanium, but may be configured using the window material 221 made of zinc selenide and the flange member 222 made of a stainless invar. Note that a thermal expansion coefficient of the stainless invar is $5.0\times10^{-6}$/K. Even when a combination of these materials is adopted, it can be seen that no cracks are generated in the window material as illustrated in FIG. 6.

Furthermore, the window forming member 22 may be configured using the window material 221 made of sapphire and the flange member 222 made of titanium or stainless invar.

Moreover, the window forming member 22 may be configured using the window material 221 made of barium fluoride ($BaF_2$) and the flange member 222 made of stainless or nickel. Note that a thermal expansion coefficient of barium fluoride ($BaF_2$) is $18.1\times10^{-6}$/K, a thermal expansion coefficient of stainless (SUS316) is $16.0\times10^{-6}$/K, and a thermal expansion coefficient of nickel is $13.3\times10^{-6}$/K.

A transmission wavelength of zinc selenide is 0.5 µm to 22 µm, and a transmission wavelength of barium fluoride is 0.15 µm to 12 µm, and both of them transmit infrared rays having a long wavelength (for example, 7 µm or more), which contributes to analysis in a long wavelength range.

In the above embodiment, the window material 221 and the flange member 222 are atomically diffusion-bonded, but these members may be bonded by, for example, welding, soldering, brazing, an adhesive, anodic bonding, or the like, or a surface activation method may be applied in which the respective members are bonded by surface activation by ion milling or the like.

Moreover, in the above embodiment, the Au thin film is adopted as the metal thin film M used for atomic diffusion bonding, but the metal thin film is not limited thereto, and may be, for example, a thin film made of Al, Cr, or the like.

The optical measurement cell 2 of the embodiment has the pair of light transmission windows W1, W2, but may have one light transmission window. In this case, light is incident on and emitted from one light transmission window. Furthermore, the optical measurement cell 2 may have three or more light transmission windows.

In the above embodiment, the joint support part 222a and the flange part 222b are integrally formed, but they may be formed as separate parts.

The window material 221 of the above embodiment has a circular shape in a plan view, but may have another shape such as a rectangular shape in a plan view.

In addition, the gas analyzer of the above embodiment uses the non-dispersive infrared absorption method (NDIR), but may use Fourier transform infrared spectroscopy (FTIR) or an optical analysis method using light other than infrared light. Furthermore, the optical analyzer of the present invention may analyze a liquid in addition to analyzing a gas as a sample.

In addition, various modifications and combinations of the embodiments may be made without departing from the gist of the present invention.

DESCRIPTION OF REFERENCE NUMERALS 100 gas analyzer (optical analyzer)
2 optical measurement cell
3 light irradiation unit
4 light detection unit
5 concentration calculation unit
W1, W2 light transmission window
221 window material
222a joint support part
222b flange part
T1 joint surface
M metal thin film

What is claimed is:

1. An optical measurement cell including a light transmission window through which light is transmitted, and into which a sample is introduced, the optical measurement cell comprising:
    a window material forming the light transmission window; and
    a flange member to which the window material is bonded via a metal thin film, wherein
    a ratio of a thermal expansion coefficient of the flange member to a thermal expansion coefficient of the window material is 0.5 times or more and 1.5 times or less.

2. The optical measurement cell according to claim 1, wherein the window material is made of zinc selenide or sapphire, and the flange member is made of titanium or stainless invar.

3. The optical measurement cell according to claim 1, wherein the window material is made of barium fluoride, and the flange member is made of stainless or nickel.

4. An optical analyzer comprising:
the optical measurement cell according to claim 1;
a light irradiation unit that irradiates the optical measurement cell with light;
a light detection unit that detects light transmitted through the optical measurement cell; and
a concentration calculation unit that calculates a component concentration in the sample using a light intensity signal obtained by the light detection unit.

5. A method of manufacturing an optical measurement cell including a light transmission window through which light is transmitted and into which a sample is introduced,
the light transmission window including a window material and a flange member supporting the window material, and a ratio of a thermal expansion coefficient of the flange member to a thermal expansion coefficient of the window material being 0.5 times or more and 1.5 times or less,
the method comprising performing atomic diffusion bonding of the window material and the flange member.

6. A window forming member used in an optical measurement cell into which a sample is introduced, the window forming member comprising:
a window material forming a light transmission window through which light is transmitted; and
a flange member to which the window material is bonded via a metal thin film,
wherein a ratio of a thermal expansion coefficient of the flange member to a thermal expansion coefficient of the window material is 0.5 times or more and 1.5 times or less.

* * * * *